(12) United States Patent
Brown et al.

(10) Patent No.: US 6,500,107 B2
(45) Date of Patent: Dec. 31, 2002

(54) METHOD FOR THE CONCENTRATION OF FLUID-BORNE PATHOGENS

(75) Inventors: Richard I. Brown, Northbrook, IL (US); Kyungyoon Min, Gurnee, IL (US)

(73) Assignee: Baxter International, Inc., Deerfield, IL (US)

( * ) Notice: Subject to any disclaimer, the term of this patent is extended or adjusted under 35 U.S.C. 154(b) by 0 days.

(21) Appl. No.: 09/874,731

(22) Filed: Jun. 5, 2001

(65) Prior Publication Data

US 2002/0183185 A1 Dec. 5, 2002

(51) Int. Cl.$^7$ ................................................. B01D 21/26

(52) U.S. Cl. ........................... 494/37; 494/45; 366/130

(58) Field of Search .............................. 494/17, 18, 21, 494/27, 29, 30, 37, 45; 366/130, 348

(56) References Cited

U.S. PATENT DOCUMENTS

| | | | |
|---|---|---|---|
| 2,598,595 A | * | 5/1952 | Peters |
| 3,217,982 A | | 11/1965 | Wilsmann et al. |
| 3,347,454 A | * | 10/1967 | Bellamy, Jr. et al. |
| 3,419,258 A | * | 12/1968 | Ritchie |
| 3,672,564 A | * | 6/1972 | Schultz et al. |
| 4,010,894 A | | 3/1977 | Kellogg et al. |
| 4,094,461 A | | 6/1978 | Kellogg et al. |
| 4,174,637 A | | 11/1979 | Mulzet et al. |
| 4,217,418 A | | 8/1980 | McAleer et al. |
| 4,386,730 A | | 6/1983 | Mulzet |
| 4,387,848 A | | 6/1983 | Kellogg et al. |
| 4,419,089 A | | 12/1983 | Kolobow et al. |
| 4,430,072 A | | 2/1984 | Kellogg et al. |
| 4,439,178 A | | 3/1984 | Mulzet |
| 4,447,221 A | | 5/1984 | Mulzet |
| 4,468,219 A | | 8/1984 | George et al. |
| 4,525,515 A | | 6/1985 | Peignier et al. |
| 4,569,759 A | | 2/1986 | Ben Aim et al. |
| 4,647,279 A | | 3/1987 | Mulzet et al. |
| 4,674,962 A | | 6/1987 | Gardineer |
| 4,708,712 A | | 11/1987 | Mulzet |
| 4,734,089 A | | 3/1988 | Cullis |
| 4,795,314 A | | 1/1989 | Prybella et al. |
| 4,810,090 A | | 3/1989 | Boucher et al. |
| 4,816,149 A | | 3/1989 | Wekell |
| 4,824,339 A | | 4/1989 | Bainbridge et al. |
| 4,850,995 A | | 7/1989 | Tie et al. |
| 4,861,242 A | | 8/1989 | Finsterwald |
| 4,894,050 A | | 1/1990 | Kohlstette et al. |
| 4,900,298 A | | 2/1990 | Langley |

(List continued on next page.)

FOREIGN PATENT DOCUMENTS

| | | |
|---|---|---|
| EP | 0 420 153 | 4/1991 |
| WO | WO 90/10057 | 9/1990 |

OTHER PUBLICATIONS

Berk et al., "Separation Of Small Ciliate Protozoa From Bacteria By Sucrose Gradient Centrifugation," *Applied And Environmental Microbiology*, pp. 450–452, Mar. 1976.

Holman et al., "Recovery Of *Giardia* Cysts From Water: Centrifugation vs Filtration," *Water Res.*, vol. 17, No. 11, pp. 1705–1707, 1983.

Kang et al., "Biological Aerosols: A Review Of Airborne Contamination And Its Measurement In Dairy Processing Plants," *Journal Of Food Protection*, vol. 52, No. 7, pp. 512–524, Jul. 1989.

(List continued on next page.)

*Primary Examiner*—Charles E. Cooley
*Assistant Examiner*—David Sorkin
(74) *Attorney, Agent, or Firm*—Gary W. McFarron; Bradford R. L. Price

(57) ABSTRACT

Methods and apparatus for concentrating and recovering pathogens from a fluid other than blood are disclosed. The method includes concentrating the pathogens contained in the fluid by continuously feeding the fluid through one or more flexible chamber(s) and subjecting the chamber(s) to centrifugal forces. The concentrated pathogens may be re-suspended by shaking the chamber(s).

15 Claims, 7 Drawing Sheets

U.S. PATENT DOCUMENTS

| | | | |
|---|---|---|---|
| 4,978,446 | A | 12/1990 | Lobdell |
| D314,824 | S | 2/1991 | Moon |
| 4,991,743 | A | 2/1991 | Walker |
| 5,100,372 | A | 3/1992 | Headley |
| 5,160,633 | A | 11/1992 | Hong et al. |
| 5,197,939 | A | 3/1993 | Cederkvist et al. |
| 5,217,427 | A | 6/1993 | Cullis |
| 5,263,831 | A | 11/1993 | Kappus |
| 5,324,629 | A | 6/1994 | Phi-Wilson et al. |
| 5,352,371 | A | 10/1994 | Felt |
| 5,356,365 | A | 10/1994 | Brierton |
| 5,427,695 | A * | 6/1995 | Brown |
| 5,496,265 | A | 3/1996 | Langley et al. |
| 5,496,301 | A | 3/1996 | Hlavinka et al. |
| 5,547,453 | A | 8/1996 | Di Perna |
| 5,571,068 | A | 11/1996 | Bacehowski et al. |
| 5,618,105 | A * | 4/1997 | Baker |
| 5,846,439 | A | 12/1998 | Borchardt et al. |
| 5,858,251 | A | 1/1999 | Borchardt et al. |
| 5,961,846 | A | 10/1999 | Borchardt et al. |
| 6,183,407 | B1 | 2/2001 | Hallgren et al. |

OTHER PUBLICATIONS

Ditrich et al., "The First Finding Of *Cryptosporidium baileyi* In Man," *Parasitology Research*, vol. 77, pp. 44–47, 1991.

Gornik et al., "Nachweismethode Und Vorkommen Von Cryptosporidium Sp. In Ausgewählten Oberflächenwässern," *Zbl. Hyg.*, vol. 192, pp. 124–133, 1991.

Whitmore et al., "Comparison Of Methods For Recovery Of *Cryptosporidium* From Water," *Wat. Sci. Tech.*, vol. 27, No. 3–4, pp. 69–76, 1993.

Johnson et al., "DNA Probe Hybridization And PCR Detection Of *Cryptospordium* Compared To Immunofluoroescence Assay," (Abstract), *Wat. Sci. Tech.*, vol. 27, No. 3–4, p. 77, 1993.

Moss et al., "Proliferative Responsiveness Of Lymphocytes From *Cryptosporidium Parvum*–exposed Mice To Two Separate Antigen Fractions From Oocysts," *Am. J. Trop. Med. Hyg.*, vol. 49, No. 3, pp. 393–401, 1993.

Starink et al., "Quantitative Centrifugation To Extract Benthic Protozoa From Freshwater Sediments," *Applied And Environmental Microbiology*, vol. 60, No. 1, pp. 167–173, Jan. 1994.

Clancy et al., "Commercial Labs: How Accurate Are They?," *Journal Amer. Water Works Association*, vol. 86, pp. 89–97, 1994.

Juranek, "Cryptosporidiosis: Sources Of Infection And Guidelines For Prevention," *CID 1995*, vol. 21 (Suppl 1), pp. S57–61, 1995.

$95^{th}ASM$ *General Meeting*, Q–212, Wed., Seesion 176, p. 437, 1995.

Nieminski et al., "Comparison Of Two Methods For Detection Of *Giardia* Cysts And *Cryptosporidium* Oocysts In Water," *Applied And Environmental Microbiology*, vol. 61, No. 5, pp. 1714–1719, May 1995.

Centers For Disease Control And Prevention. "Assessing The Public Health Threat Associated With Waterborne Cryptosporidiosis: Report Of A Work–shop," *MMWR*, vol. 44, No. RR–6, pp. 1–19 (minus 17), Jun. 16, 1995.

Goldstein et al., "Cryptosporidiosis: An Outbreak Associated With Drinking Water Despite State–Of–The–Art Water Treatment," *Annals Of Internal Medicine*, vol. 124, No. 5, Mar. 1, 1996.

*Cryptosporidium Capsule*, vol. 1, Issue 6, pp. 1–12, Apr. 1996.

Colford et al., "Cryptosporidiosis Among Patients Infected With Human Immunodeficiency Virus," *American Journal Of Epidemiology*, vol. 144, No. 9, Nov. 1, 1996.

Guarino et al., "Enteric Cryptosporidiosis In Pediatric HIV Infection," *Journal Of Pediatric Gastroenterology And Nutrition*, vol. 25, No. 2, pp. 182–187, 1997.

Selik et al., "Effect Of The Human Immunodeficiency Virus Epidemic On Mortality From Opportunistic Infections In the United States In 1993," *The Journal Of Infectious Diseases*, vol. 176, pp. 632–636, Sep. 1997.

Pozio et al., "Clinical Cryptosporidiosis And Human Immunodeficiency Virus (HIV)—Induced Immunosuppression: Findings From A Longitudinal Study Of HIV–Positive And HIV–Negative Former Injection Drug Users," *The Journal Of Infectious Diseases*, vol. 176, pp. 969–975, Oct. 1997.

Hoxie et al., "Cryptosporidiosis–Associated Mortality Following A Massive Waterborne Outbreak In Milwaukee, Wisconsin," *American Journal Of Public Health*, vol. 87, No. 12, pp. 2032–2035, Dec. 1997.

Marshfield Clinic. "Cryto Immune" pp. 2 of 2, 1998.

Marshfield Clinic. Excerpt from "Helix Water District's 1996 Water Quality Report," p. 2 (of 5), 1998.

* cited by examiner

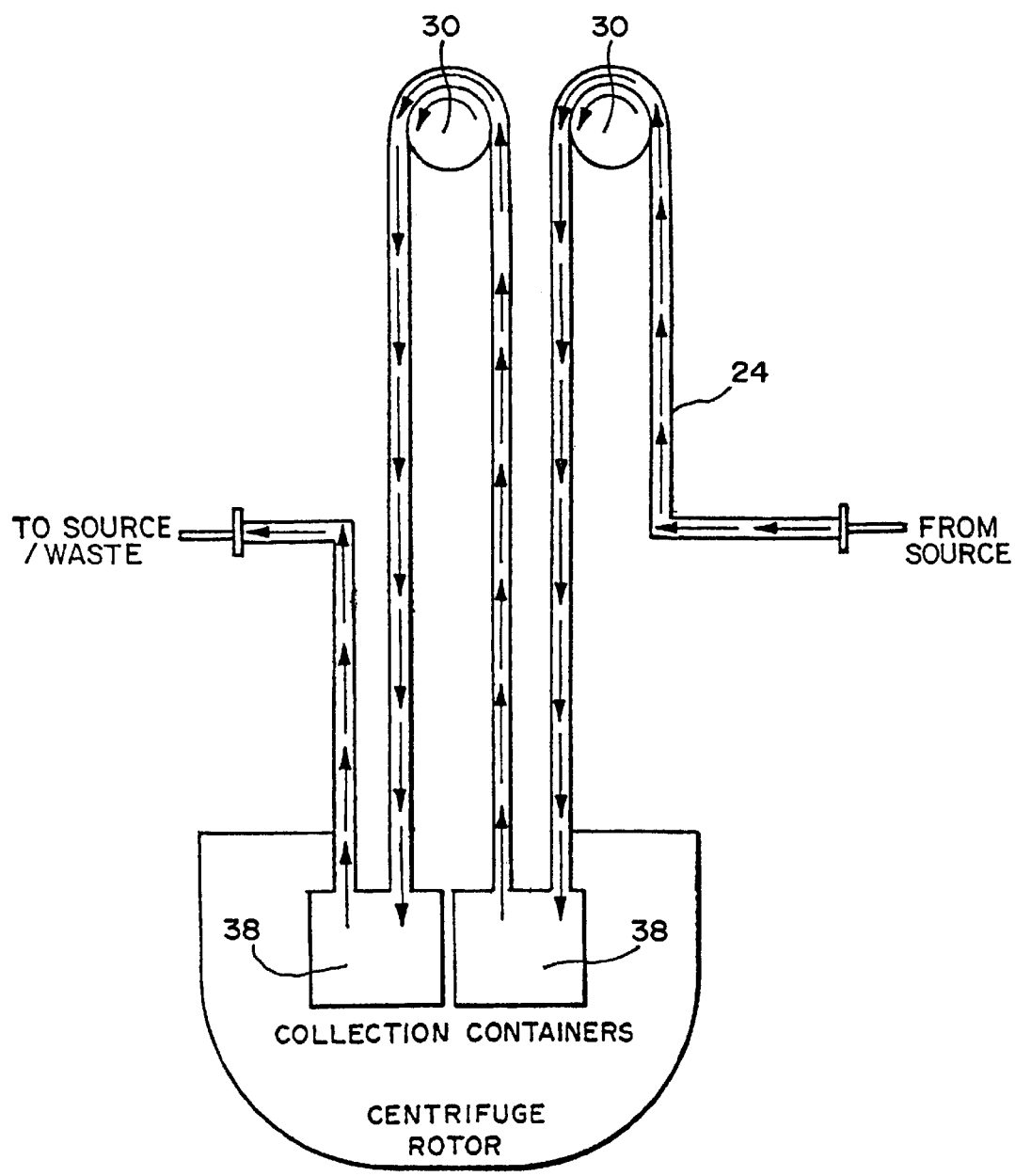

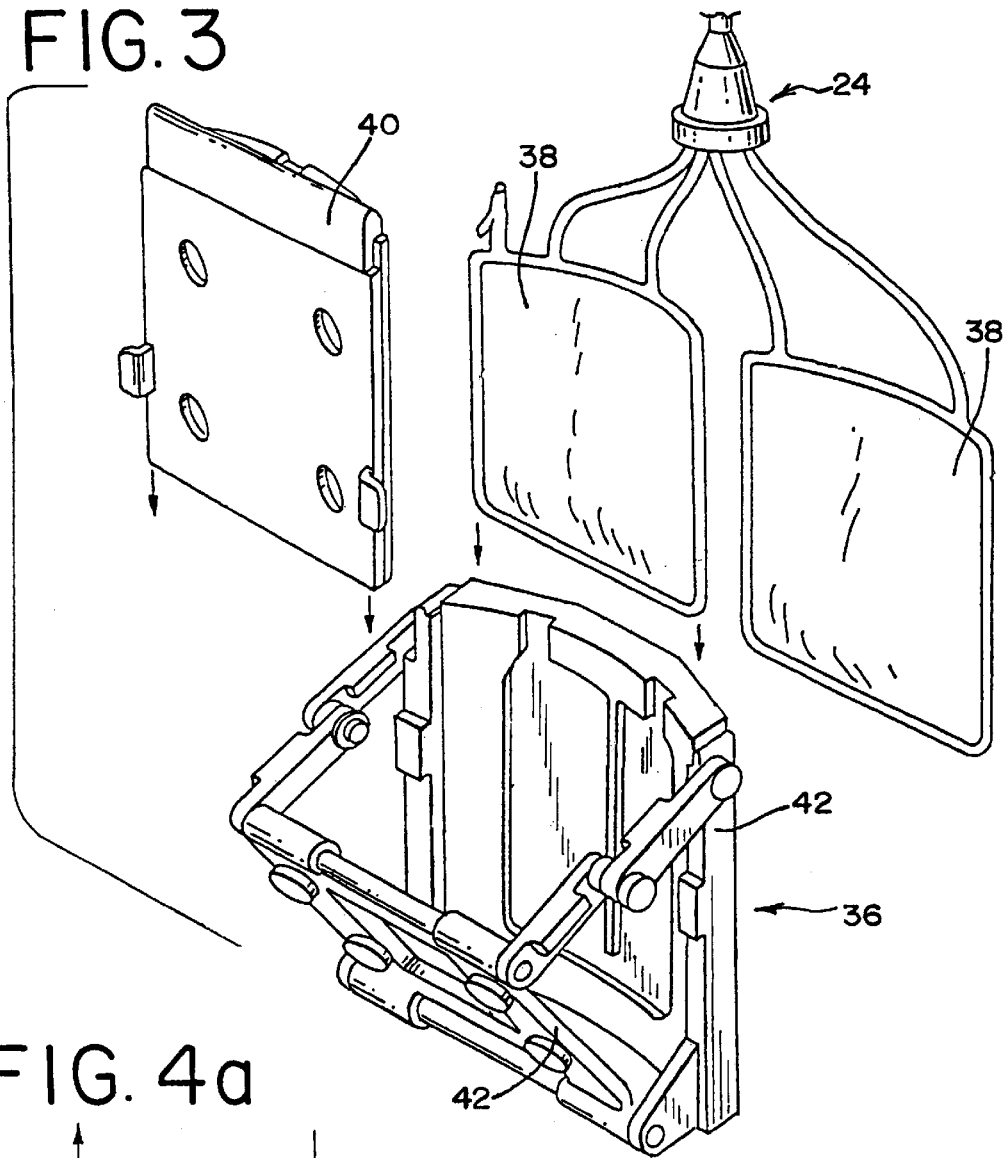
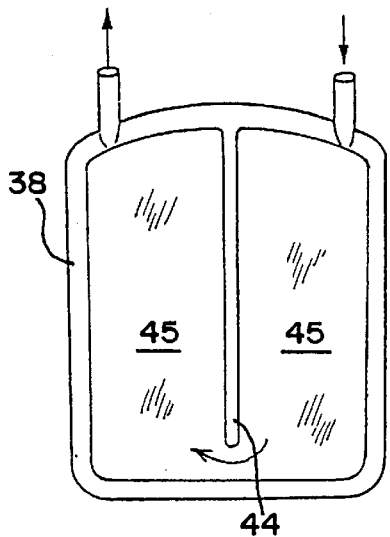
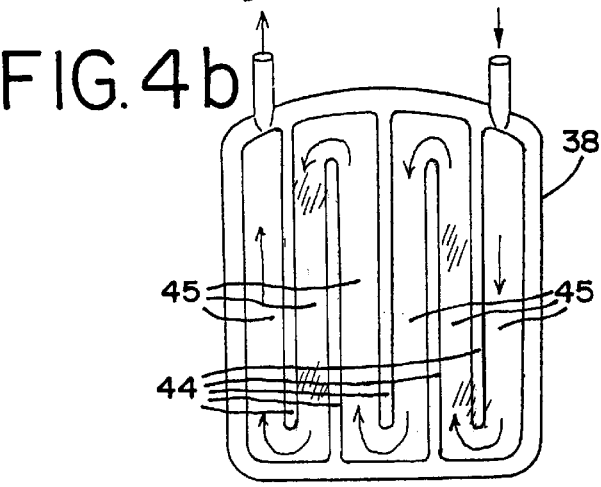

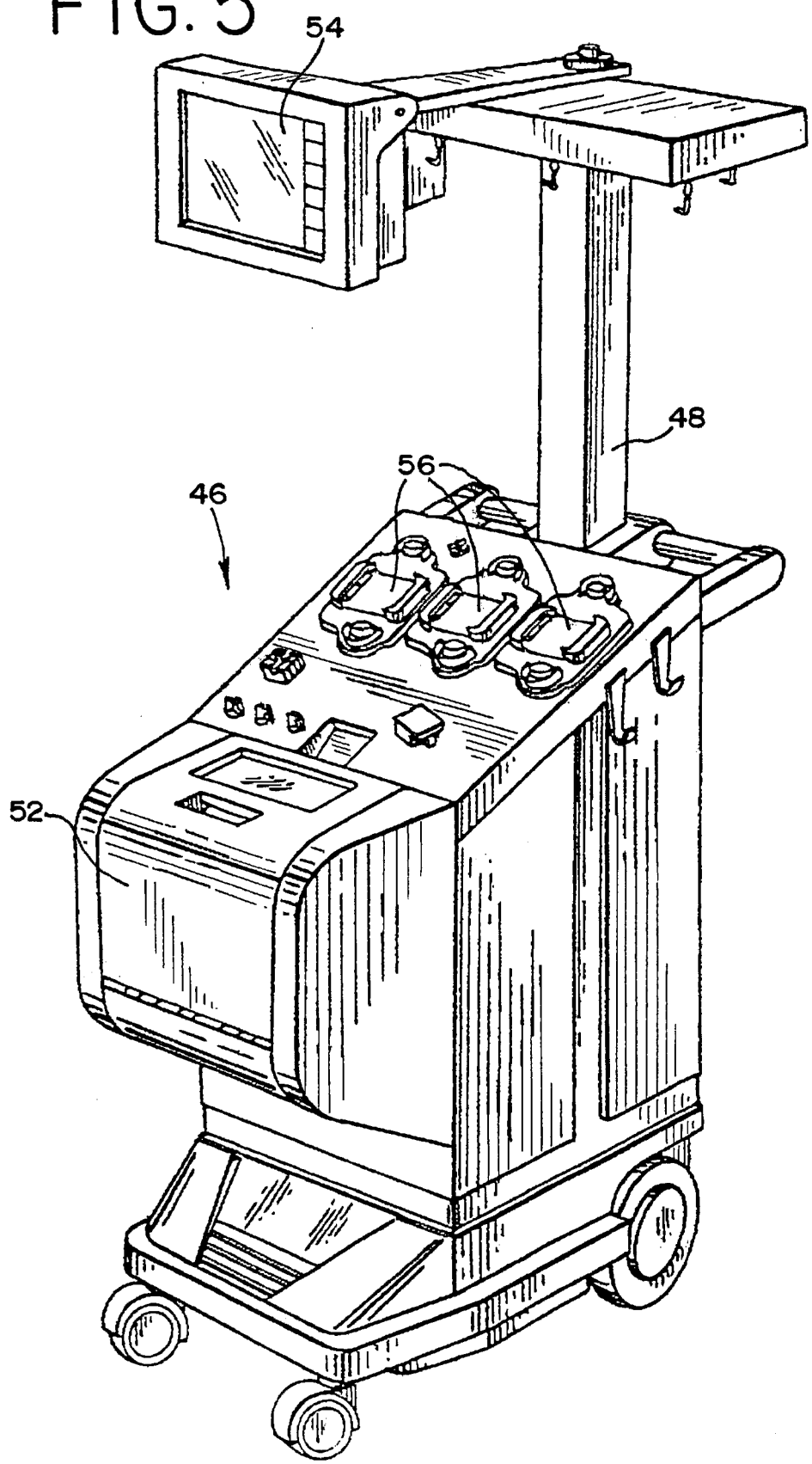

METHOD FOR THE CONCENTRATION OF FLUID-BORNE PATHOGENS

The present invention relates to method and apparatus for concentrating fluid-borne pathogens from fluids potentially containing such pathogens. More specifically, the present invention relates to methods and apparatus for concentrating pathogens in a centrifugal chamber and for re-suspending them to permit withdrawal of the concentrated pathogens from the chamber for testing, quantifying and the like.

It is known to use centrifuges for the purpose of concentrating water and food-borne microorganisms, particularly pathogens including Clostridium, Streptococcus, Shigella, Salmonella, and other species, as set forth in U.S. Pat. Nos. 5,961,846; 5,858,251; and 5,846,439, all of which are hereby incorporated by reference into this description. These patents disclose a technique for flowing large quantities of water or fluidized foods through a semi-rigid belt channel in a blood centrifuge, such as the IBM Model 2997 or the Cobe Spectra centrifuge, to concentrate any microorganisms contained in the fluid.

These centrifuges employ a disposable annular or circumferential separation chamber that is mounted on a reusable hardware platform. The centrifuge rotates the separation channels as fluid flows through the channel, concentrating microorganisms within the channel. In order to test, identify or otherwise evaluate any pathogens or other microorganisms concentrated in the channel at the end of the process, the disposable channel must be removed from the centrifuge device, and any pathogens or other microorganisms contained therein must be flushed from the channel.

Although the centrifuges may work satisfactorily for concentrating fluid-borne microorganisms, the steps of re-suspending and removing concentrated pathogens from the centrifuge separation channel have presented some difficulty, and the above-identified patents describe a relatively complex technique for recovery of the channel contents after the centrifugation process has ended. First, according to the '439 patent, the separation channel is primed with water containing a surfactant to enhance removal of the material later collected. In addition, after the centrifugation is completed, and the contents of the separation channel are drained into a beaker, the channel is then cut in half and filled with a solution of surfactant. The cut ends are clamped with Vise-Grip® pliers, and the channel is shaken vigorously and placed in a laboratory vortex to dislodge pathogens that may have adhered to the inner walls of the channel. This rinsing procedure is conducted several times, and the concentrate and all the rinses are combined.

The disposable centrifuge channels used in the IBM 2997 and COBE Spectra centrifuges are made of semi-rigid, somewhat brittle, plastic material, which is not conducive to repeated flexing or the like. This may have contributed to the difficulty in removing concentrated pathogens from the channel and necessitated the use of surfactant, Vise-Grip pliers and a laboratory vortex to aid in removing the concentrated microorganisms. Also, the presence of other residue in the channel may have made removal of the microorganisms more difficult. The present invention is intended to overcome one or more of the shortcomings associated with the prior art devices and methods. As used in the following description and claims, "fluid" (and formatives thereof) means any liquid, excluding blood, blood cells, plasma or other blood components, that flows sufficiently for continuous centrifugal processing, and "pathogens" and "pathogenic organisms" (and formatives thereof) mean a disease-causing or abnormality-causing organism and do not include, in any event, blood cells such as red cells, white cells and platelets.

SUMMARY

The present invention is generally embodied in method and apparatus for concentrating and recovering pathogens from fluid by employing a flexible centrifugation chamber, through which the fluid is continuously flowed. The flexible centrifugation chamber is subjected to centrifugal force by rotating the chamber about an axis of rotation while fluid is being fed therethrough, so as to concentrate in the chamber pathogens that may be contained in the fluid. In accordance with the present invention, the flexibility of the chamber enhances re-suspension of pathogens that are concentrated therewithin, and the pathogens may be re-suspended by shaking the flexible chamber with fluid contained therein. By vigorously shaking the container to and fro, the fluid therein is caused to slosh from end to end by virtue of the flexibility of the chamber. This induces high shear stresses and promotes re-suspension of the pathogens. The flexible chamber may also be stretched such that the gap of the chamber can be adjusted. By doing this, one can induce and control proper shear stress. This can be done manually or automatically.

The step of shaking the chamber may be carried out manually or automatically and may include squeezing and/or twisting of the chamber to cause the fluid to slosh back and forth.

The flexible centrifugation chamber may be elongated, and fluid may be introduced into the chamber substantially at one end and withdrawn substantially at the other end of chamber. Alternatively or additionally, the chamber may be subdivided into a series of interconnected flow channel segments so that fluid repeatedly substantially traverses the length or width of the container as it passes therethrough, thereby decreasing stagnation or unperfused areas of the chamber and resulting in a more uniform flow field in the centrifugal field, and thus enhancing concentration of pathogens in the chamber. Other serpentine flow path arrangements may also be used within the flexible chamber.

In accordance with the present invention, a single centrifuge chamber may be used in the concentration procedure. Also, multiple chambers, formed of entirely separate chambers or formed from a single disposable unit or chamber sub-divided into two or more subchambers, may be employed for higher fluid processing rates or collection efficiency. For example, the use of separate containers or sub-chambers with separate inlets connected in parallel to the fluid source may allow for higher processing rates, since fluid is simultaneously being processing through two chambers.

Also, separate chambers or sub-chambers may be connected in series for improved efficiencies. The second chamber could be used for the more specific collection of pathogens from the fluid. In other words, the supernatant from the first stage will include many of the target pathogens which can be concentrated in the second chamber or stage. For particularly small pathogens, a sedimentation enhancing agent, such as an affinity agent, for example, a chemical enzyme, may be added to the supernatant from the first chamber to enhance sedimentation of the pathogenic organisms contained therein.

In a multiple stage or multiple chamber separation, the first chamber in the series could be a simple plastic pouch, with or without a simple u-shaped or other flow path, for collection of a large volume of sediment. The second container could employ the same or a lengthier flow path, such as shown in FIG. 4a or 4b. In either the parallel or series arrangement, one chamber (container) could immediately be used for testing, identifying or quantifying the pathogens, and the other chamber could be severed, sealed and stored as an archive for future testing or reference if desired. Additional chambers (more than two) also could be employed in parallel or series in accordance with this aspect of the present invention. Also, in the series arrangement, the first chamber could include a passageway for withdrawal of concentrated particles (which may include some of the pathogens) on an intermittent or continuous basis.

The flexible centrifugation chamber may be fashioned in various different ways without departing from the present invention. In one preferred embodiment, the chamber is defined by a pair of facing sheets of flexible plastic film that are sealed together, as by heat or solvent, along at least a peripheral area to define an interior chamber for centrifugal fluid processing. Other forming techniques may also be used, provided that the end result is a flexible centrifugation chamber that may be easily deformed for re-suspension. For example, a rigid or semi-rigid chamber could be used with a flexible liner. The rigid or semi-rigid container could provide the desired shape for centrifugation purposes, and the flexible liner removed after centrifugation for easy re-suspension. Also, the chamber could be partially rigid or semi-rigid and partially flexible. The areas of the chambers where the pathogens concentrate could be made flexible, and the remainder of the chamber or container could be rigid or semi-rigid, which may be easier to shake.

In addition to the peripheral seal, other seal lines may be provided between the facing plastic sheets to define an elongated or serpentine flow path or to define a plurality of interconnected flow channel segments within the chamber to potentially improve the uniformity of the flow fields of fluid passing through the chamber and enhance the collection efficiency. These additional seal lines may be provided permanently by bonding together the facing plastic sheets, as by heat or solvent bonding, or may be provided temporarily by compressing the plastic sheets together in the desired locations to form the desired flow path configuration during centrifugation and allowing the films to separate to form a single chamber after centrifugation is complete. These are but a few of the features of the present invention found in the following more detailed description.

DESCRIPTION OF DRAWINGS

FIG. 2 is a flow diagram, illustrating the flow of fluid through the centrifuge of FIG. 1 during the concentration procedure, with the containers connected in a series arrangement.

FIG. 3 is a perspective view of a clamp and platen arrangement of the type used in the centrifuge shown in FIG. 1, for cooperation with a disposable flexible container to temporarily define a centrifugation chamber of selected configuration.

FIG. 4a is a plan view of the container depicted in FIG. 3, illustrating one configuration of the chamber as defined by the clamp and platen, in which the fluid flow path through the chamber is generally U-shaped.

FIG. 4b is a plan view of the container depicted in FIG. 3, illustrating another configuration of the chamber as may be defined by the clamp and platen, in which the fluid flow path through the chamber is generally serpentine, created by a series of interconnected flow path segments that extend vertically in the container.

FIG. 5 is a perspective view of another centrifuge that may be used in accordance with the present invention.

DETAILED DESCRIPTION

Figure 1:
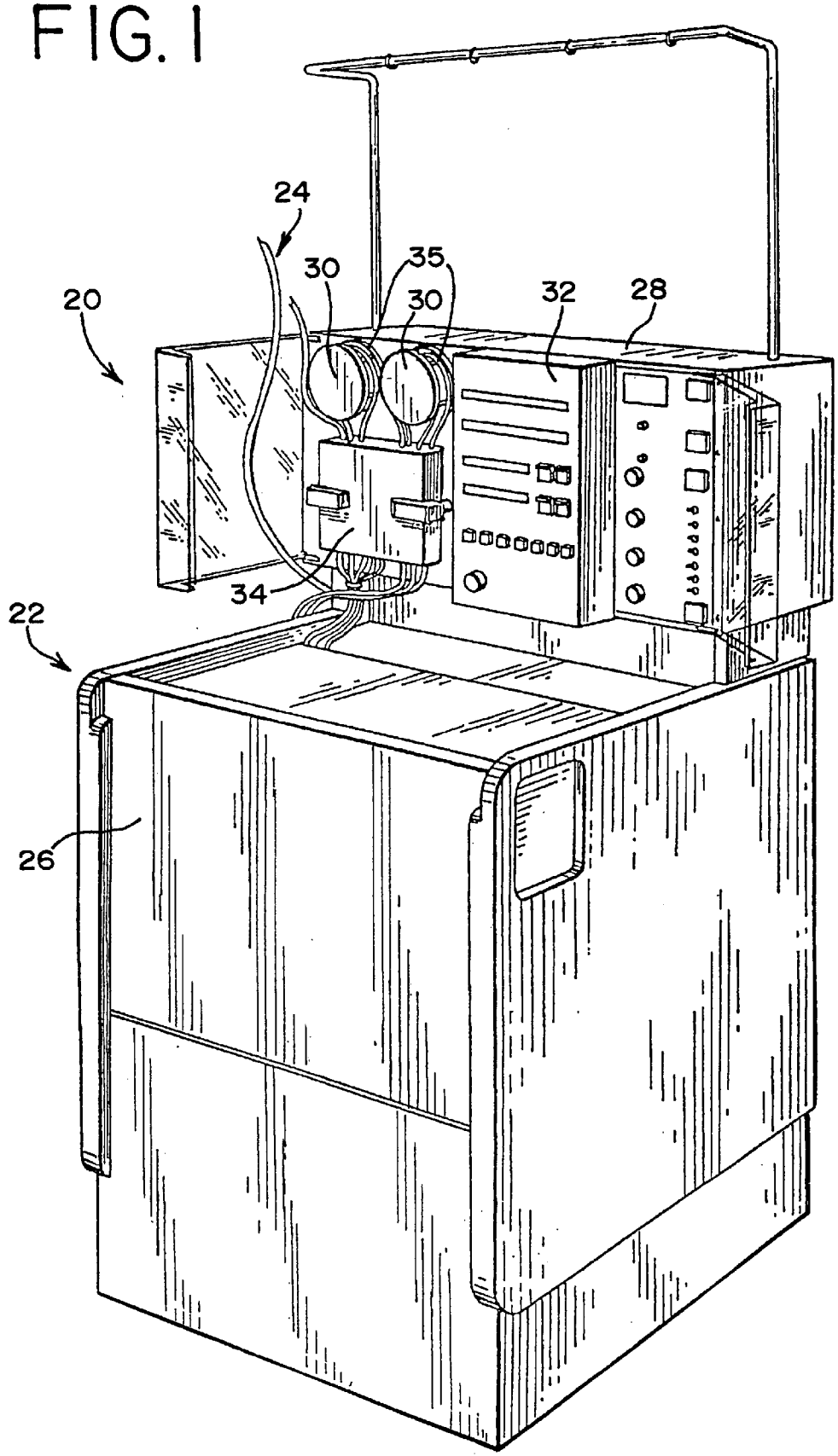
FIG. 1 is a perspective view of a centrifuge that may be used in the method of the present invention.

FIG. 1 illustrates one type of centrifuge system that may be used in carrying out the method of the present invention. Specifically, FIG. 1 shows a CS-3000® centrifuge 20 of the type that has long been manufactured and sold by the Fenwal Division of Baxter Healthcare Corporation of Deerfield, Ill. The CS-3000 centrifuge system of FIG. 1 includes a reusable hardware portion 22 and a disposable tubing set or fluid circuit 24.

The centrifuge hardware portion includes a base 26, in which the rotating portion of the centrifuge is located, and a control panel 28, which contains pumps 30, valves and detectors (not shown) and a user display and input section 32 for user control of the centrifuge operation. As described in more detail in U.S. Pat. No. 4,525,515, which is hereby incorporated by reference into this description, the disposable fluid circuit includes a control housing or monitor box 34, through which the fluid tubing is routed. The monitor box organizes the tubing for simplified installation and mounts over sensors, valves and associated devices on the control panel. Fluid flow tubing extends from and returns into the housing 34 to form external tubing loops 35 adapted to fit over a pair of peristaltic pumps 30, as seen in FIG. 1, for moving fluid through tubing set 24.

Turning next to FIG. 3, the centrifuge of FIG. 1 employs a pair of opposed clamps 36, which are orbited or rotated about an axis of rotation. Each clamp holds a flexible plastic bag 38, which forms a centrifuge chamber, which is part of the disposable fluid circuit. The disposable tubing set has two such centrifuge bags, one for each clamp.

The bags are typically in a series arrangement in the fluid circuit, and fluid flows through the bags as illustrated in FIG. 2. As shown there, fluid which may possibly be contaminated with pathogens, flows from the fluid source through tubing into a first one of the flexible centrifuge chambers formed from the bag 38. The fluid exits that chamber and is directed into a second flexible centrifuge chamber, from which it then exits for return to the source or to a waste facility such as a drain or the like.

The flow rate of fluid through the centrifuge containers is controlled by peristaltic pumps 30. Although two pumps are shown, it is more likely that only one centrifuge pump would be used to pump fluid from the source through both centrifuge chambers, when in a series arrangement. Alternatively, the bags could be arranged in parallel and each pump would draw fluid from a fluid source and direct it through one of the bags for pathogen concentration. Such a parallel processing arrangement could substantially reduce processing time for a given quantity of source fluid.

In the CS-3000 centrifuge, each bag 38 is defined into the desired centrifuge chamber shape by the respective clamp in which it is mounted. Each clamp receives a platen 40 which has raised surfaces designed to press against one side of the bag 38 to form the bag into a selected shape. The same or different platens may be used in each clamp, depending on the desired chamber configuration.

As illustrated in FIG. 3, for example, the bag 38 which forms the flexible centrifuge chamber is generally of the shape of a flat pouch, formed by peripherally sealing together two facing plastic sheets. The bag is located between hinged plates 42 of the clamp 36. A platen 40 having raised surfaces of the desired configuration, is also located between the hinged plates of the clamp 36. When the clamp is closed, the platen presses the bag 38 against one side of the clamp, compressing the facing sheets of the bag together in selected locations to form the desired configuration for the centrifuge chamber.

An example of such a chamber configuration is shown in FIG. 4a. There, the facing sheets of the bag 38 are pressed together along a vertical line 44 that extends from the upper peripheral seal to a location spaced from the lower peripheral seal. This forms a generally U-shaped flow path in the centrifuge chamber that is defined by two vertical flow path segments 45 that extend the length of the bag and are interconnected at the bottom gap between the seal line 44 and the peripheral edge of the bag.

In accordance with a further alternative of the present invention, the platen and clamp may be shaped to provide a series of such vertical seal lines 44, as shown in FIG. 4b, extending alternately from the upper and lower peripheral seals to define an elongated, serpentine flow path of greater length defined by six vertical flow path segments 45, thereby increasing the length of the flow path and potentially enhancing removal of pathogens from the fluid circulating therethrough by inducing a more uniform perfusion.

Also, the shape and direction of the flow path could be changed without departing from the present invention. The flow path segments could extend horizontally, for example, or the flow path could take other forms such as a spiral or circular arrangement to increase the length of the flow path as desired.

After the concentration procedure is complete, the bag 38 may be removed from the clamp. In the absence of the clamping pressure, the bag resumes its normal pouch-like configuration, free of the vertical or other lines of compression, allowing the bag to be vigorously shaken for improved re-suspension of pathogens concentrated in the container.

Figure 6:
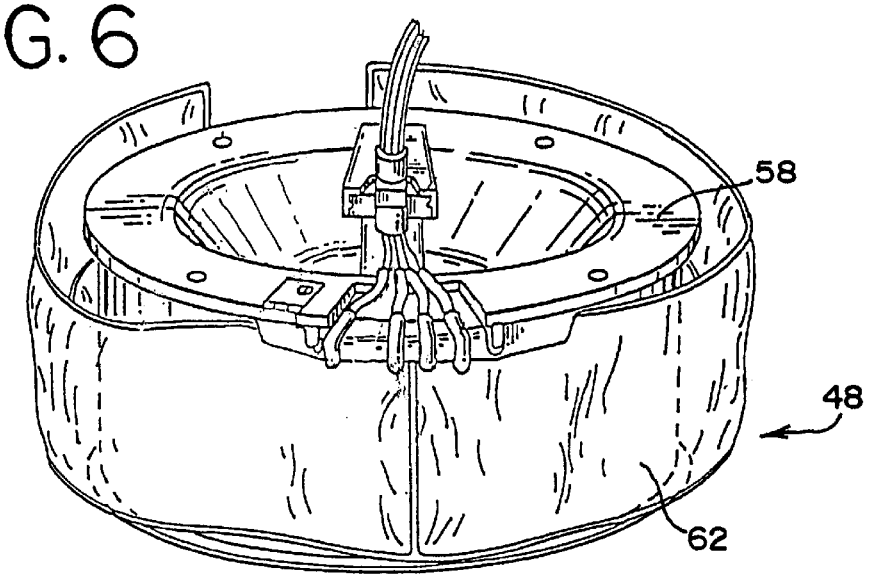
FIG. 6 is a perspective view illustrating assembly of the flexible centrifuge container on a center spool or core that is mounted within the centrifuge of FIG. 5.

FIG. 5 illustrates another type of centrifuge that may be used in connection with the present invention. The centrifuge 46 shown there is the Amicus® centrifuge, which is made and sold by Baxter Healthcare Corporation of Deerfield, Ill. The Amicus centrifuge 46 also employs a reusable hardware portion 48, shown in FIG. 5, and a disposable tubing set or fluid circuit 48, the pertinent portion of which is shown in FIG. 6.

The reusable hardware portion 48 has a base 52, in which the rotating parts of the centrifuge are contained, and an elevated control screen and user input panel 54 for operator control of the centrifuge operation. The base includes one or more pumping stations 56 that are adapted to receive a flow control cassette and various sensors and valves that cooperate with the tubing set for controlling the flow of fluid through the disposable circuit.

The Amicus centrifuge was originally designed for separation of blood and blood components, and employed three pumping stations for controlling the flow of the different fluids, such as saline, anticoagulant, whole blood, and blood complements through the fluid circuit. It is contemplated that only one or two pumping stations would be required for use of the Amicus centrifuge in connection with the present invention, although the availability of additional pumping stations adds flexibility for future applications that may not be contemplated at the present time. The Amicus centrifuge and associated disposable fluid circuit are described in more detail in U.S. Pat. No. 5,547,453, which is hereby incorporated by reference into this description.

As described more fully in the above-patent, the Amicus centrifuge employs a spool and bowl arrangement in which an inner spool 58 is located within an outer centrifuge bowl 60, and the flexible centrifuge chamber, in the form of an elongated pouch or belt 62, is located between the spool and bowl. FIG. 6 illustrates mounting of a flexible centrifuge chamber, which is in the form of a flexible plastic belt, around the outside of the spool 58. After the flexible belt is mounted on the spool, the spool and belt are placed within an outer centrifuge bowl 60. The spool and bowl are in an inverted position, as shown in FIG. 6, when operating within the centrifuge.

Fluid is introduced into the flexible centrifuge chamber and withdrawn therefrom through a flexible umbilicus 64 that connects the disposable centrifuge chamber to a stationary portion of the centrifuge. As described more fully in the above-identified patents and in U.S. Pat. No. 4,734,089, also incorporated by reference herein, both the CS-3000 and Amicus centrifuges employ the 1w–2w principle to provide a seal-less connection between the rotating centrifuge chamber and the exterior of the centrifuge device. The seal-less connection avoids the need for the rotating seal, rotating seal lubrication, and the other assorted safeguards and operational limitations associated with rotating seals in high-speed centrifuges.

Figure 8:
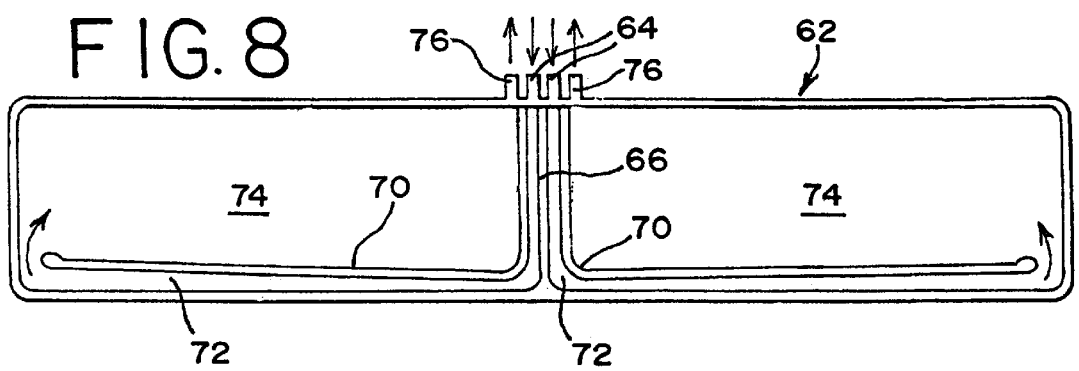
FIG. 8 is a plan view of a flexible centrifuge chamber that may be used in connection with the centrifuge shown in FIG. 5.
Figure 9:
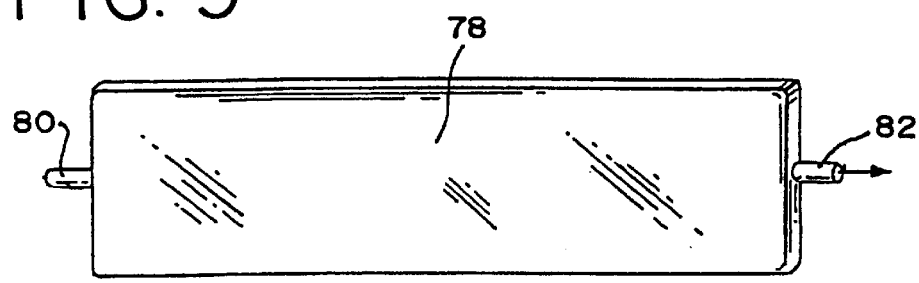
FIG. 9 is a perspective view of an alternative flexible centrifuge chamber that may be used with the centrifuge of FIG. 5.
Figure 10:
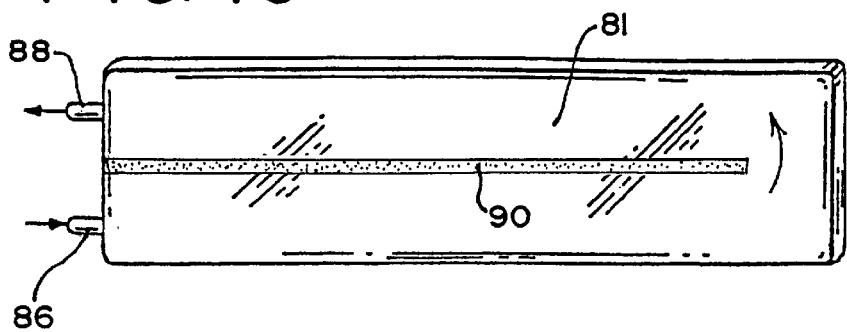
FIG. 10 is a perspective view of another alternative of the flexible centrifuge chamber that may be used in combination with the centrifuge of FIG. 5.

Various examples of the bag which may be used to define the flexible centrifuge chamber in the Amicus centrifuge are shown in FIGS. 8–10. As shown in FIG. 8, the chamber is defined by a plastic web or belt formed by two flexible plastic sheets or films peripherally sealed together, such as by heat or solvent bonding commonly used to manufacture such containers in the medical industry. A vertical seal line 66 divides the resulting pouch into two sub-chambers or sub-pouches, which may be the same or different size. An interior seal line 70 in each sub-pouch forms first and second flow segments 72 and 74 in each sub-pouch, through which fluid must flow. In the Amicus centrifuge, the seal lines are typically permanent, and formed by heat or ultrasonic bonding of the two facing plastic sheets.

The container (bag or belt) preferably has a sufficiently thin wall and is made from a material sufficiently pliable to allow ready flexing of the container walls by fluid sloshing within the container during re-suspension. One example of such a material is polyvinyl chloride (PVC) that has been plasticized with a selected amount of a plasticizer such as DEHP or a citrate ester. Also the interior surface of the facing sheets forming the belt may be embossed to provide a slightly roughened surface. This serves to prevent the sheets from adhering together and allowing separation of the sheets when fluid is introduce. In addition the roughened surface creates numerous microscopic barriers that may serve to trap the very small pathogens and retard their movement along the surface of the container and eventual re-entrainment in the fluid circulating through the chamber. The result may be increased pathogen capture and concentration efficiency.

As shown in FIG. 8, the seal line 70 is L-shaped, and has a vertical portion that extends generally parallel to seal line 66 and a substantially horizontal portion that is spaced from the lower edge of the belt and terminates just short of the end wall of the belt to interconnect the flow segments and allow fluid to flow. Fluid thus flows into an inlet 64 in each sub-pouch, through the first segment 72, around the end of the horizontal seal line and into and through the second segment 74 and through outlet 76. In this arrangement, the fluid must flow substantially along the length of the sub-chamber twice, and fluid cannot "short-cut" between the inlet and outlet, which would reduce the residence time in the centrifugal field and the concentration efficiency.

As discussed earlier in connection with the separate bags used in the CS-3000 centrifuge, the subchambers of the Amicus disposable belt may be connected in parallel or series and may be of the same or different sizes. The subchambers may be free of any interior seal, or additional seal lines may be used to create a more uniform flow path or field within one or both flow chambers, or any combination of these.

FIG. 9 is an alternative centrifuge chamber defined by a flexible plastic belt 78 that is elongated, generally rectangularly shaped, with an inlet 80 at one end and an outlet 82 at the other end.

FIG. 10 illustrates yet a further embodiment a flexible centrifuge chamber defined by a plastic bag or belt 84 in which both inlet 86 and outlet 88 are at the same end of the flexible plastic container, and an intermediate horizontal seal line 90 extends from one end of the container to a location spaced from the other end to form the container into first and second flow interconnected flow segments so that the fluid must traverse the length of the container twice before exiting through the outlet. As with the embodiment described in the CS 3000, additional intermediate seal lines may be provided to define any desired number of additional interconnected flow path segments so that fluid passing through the bag is required to traverse the length or width of the bag at least 4 and perhaps as many as 8 or more times.

Figure 7:
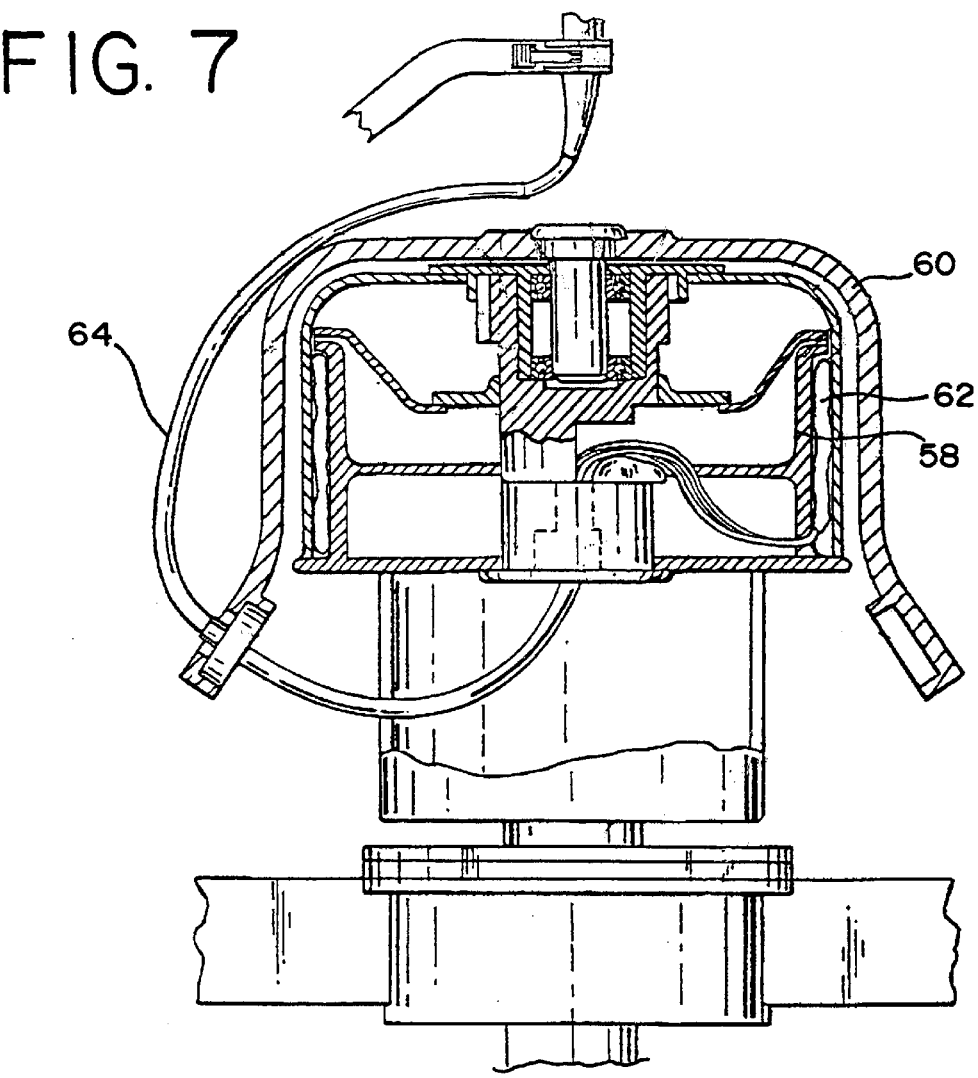
FIG. 7 is a cross-sectional view of the centrifuge illustrated in FIG. 5, and showing the flexible container and center spool mounted within an outer bowl for rotation within the centrifuge.
Figure 11:
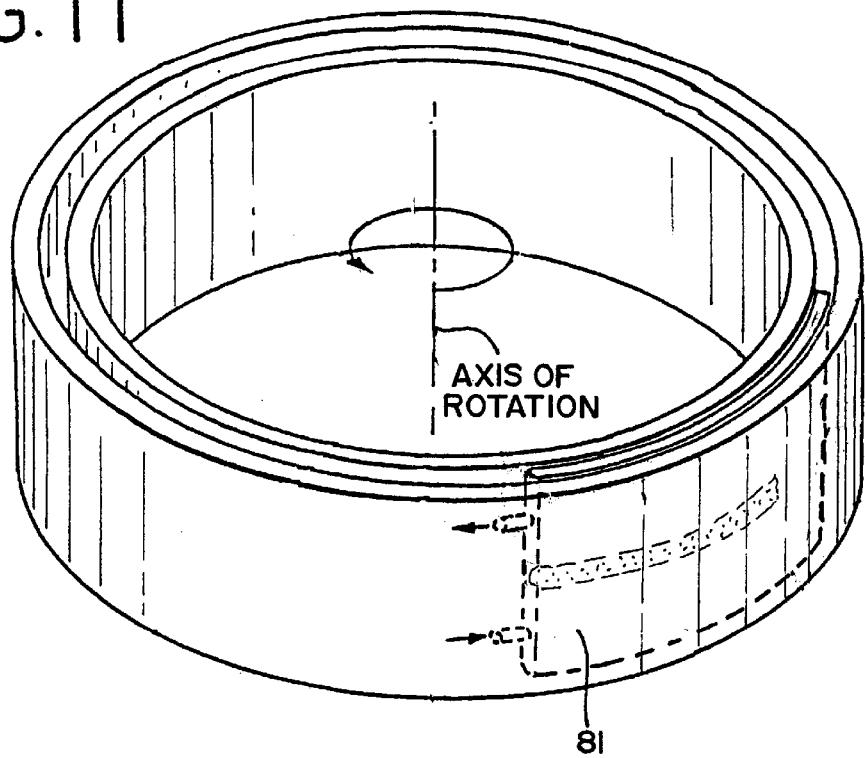
FIG. 11 is a diagrammatic view, depicting rotation of a flexible centrifuge chamber in a centrifuge of a type generally shown in FIG. 5.

FIG. 11 is a diagrammatic illustration of the container of FIG. 10 in the Amicus centrifuge. As shown there, the container 84 is located between an inner wall, which is defined by the spool 58, and an outer wall which is defined by bowl 60, as best shown in FIG. 7. Together they are rotated about an axis of rotation, subjecting the bag and its contents to a centrifugal field which tends to force the particles in the fluid, including pathogenic organisms, toward the outermost wall of the container where they can be concentrated.

In accordance with the method of the present procedure, potentially contaminated fluid is flowed continuously through the flexible centrifuge chamber or chambers located in the centrifuge. As apparent from the illustrated examples, the centrifuge chamber may be a single chamber, may be separate chambers, or may be a single chamber that is subdivided into sub-chambers or sub-pouches. Fluid may flow directly from inlet to outlet of the chamber or through a lengthier, such as a serpentine channel, which requires the fluid to traverse the length or width of the chamber 2 or more times.

The centrifugal field or force selected may be the choice of the user. Typically, however, it is believed that centrifugal field generated by rotation of 1000–6000 rpm, with the centrifuge chamber located at a radius of from about 1–6 inches from the axis of rotation should provide sufficient centrifugal force to result in concentration of pathogenic organisms that may be contained within the fluid.

After a selected amount of fluid is processed through the centrifugal chamber, the chamber, i.e., bag, belt or pouch, is removed from the centrifuge, preferably but not necessarily with a quantity of fluid contained therein. The chamber is then shaken vigorously to and fro to re-suspend within the fluid any pathogenic organisms that have been concentrated in the chamber. The highly flexible and deformable container that is employed in both the CS 3000 and Amicus centrifuges allows the fluid therein, in effect, to slosh back and forth from end to end, thus creating high shear stresses that help re-suspend the pathogens that have been concentrated within the chamber. Unlike the prior art semi-rigid chambers of the IBM 2997 and Cobe Spectra centrifuges, it is unnecessary to apply Vise-Grip pliers to the centrifuge chamber or to subject the chamber to unique and time-consuming procedures to re-suspend the pathogens that have been concentrated into the container.

Figure 12:
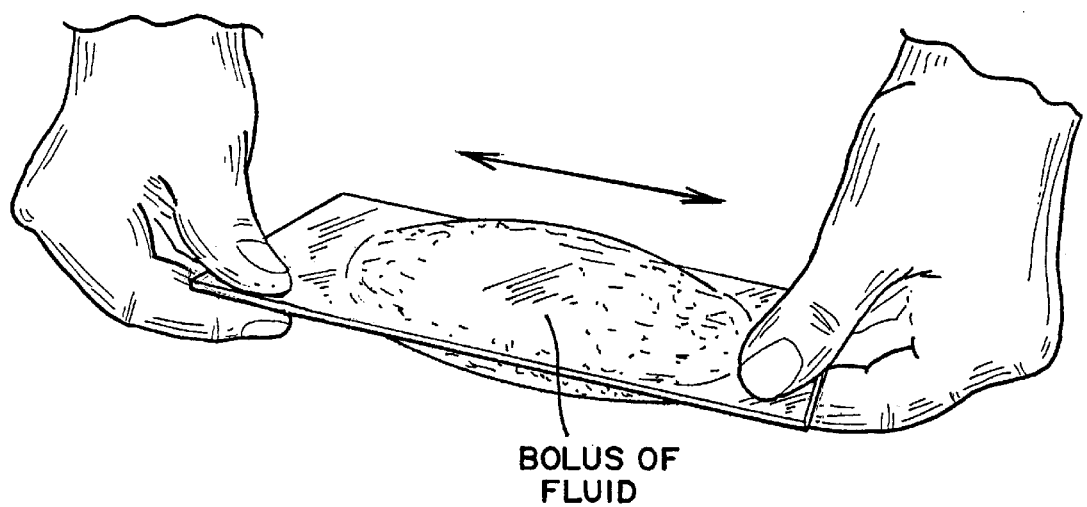
FIG. 12 is a perspective view illustrating the to and fro, or lengthwise shaking that may be used in the process of the present invention to re-suspend pathogens that are concentrated in the flexible centrifuge chamber.

As shown in FIG. 12, the shaking of the container may be carried out manually and may include twisting the container. During re-suspension, the chamber (belt or bag) is held at both ends and vigorously shaken to and fro (longitudinally). For example, shaking the belt or bag to and fro can be achieved by grasping the belt or bag at its ends (as generally depicted in FIG. 12) and shaking the chamber from side to side, or holding the chamber in a vertical position and shaking it up and down. Whether shaken horizontally, vertically or in another direction ("to and fro" includes any of these), the inertia of the fluid contained within the chamber tends to concentrate the fluid in a central mass or bolus, as depicted by the bulging flexible container walls in FIG. 12, that remains essentially stationary as the walls of the bag move past, thereby causing high shear stresses on the pathogens to help dislodge them from the surfaces. Relative to the chamber, the fluid appears to slosh back and forth one end to the other. In addition to the high shear stresses established, the apparent sloshing causes the flexible chamber to deform flexibly with each cycle of shaking and may further help to dislodge the pathogens. Prior art rigid or semirigid containers do not deform sufficiently for the fluid to build into a central mass and thus cannot establish the high fluid stress induced in the flexible chamber employed here.

The shaking could also be carried out automatically, and different chamber configurations could be used to permit shaking. For example, the centrifuge itself could be used to shake the bag or belt that forms the chamber, or an external device could be used. If the centrifuge itself is used to "shake" the bag for re-suspension purposes (after the pathogen concentrated procedure is completed), the centrifuge could employ a pneumatic device to repeatedly push on the belt wall radially, sloshing the fluid back and forth within the belt. For purposes of illustration, this could be a pneumatic device or balloon or a series of such devices or balloons located around the inside surface of the bowl in the Amicus centrifuge, which could be rapidly and repeatedly inflated against the belt wall to cause sloshing of fluid therein to re-suspend the pathogens automatically. This also could be combined with vibrating motion of the centrifuge, not necessarily along the rotational axis, to aid in the re-suspension.

After shaking, the contents of the container are drained into a beaker or other receptacle. Thereafter, rinse solution, such as distilled water, may be added to the container, and the shaking step repeated to insure that the re-suspended pathogenic organisms are fully flushed from the container. Alternatively, distilled water may be added to the container before the initial shaking to re-suspend any pathogens concentrated in the container.

As pointed out earlier, separate processing chambers or sub-chambers may be connected in series or parallel for better flow rates and/or efficiencies, as well as to provide additional features. In this regard, the first container in the series could be simple pouch or employ a simple u-shaped flow path or the like, and the second container could employ the same or a longer flow path, such as shown in FIG. 4b for example. The first container in this arrangement, which also may contain some concentrated pathogens, could be severed from the fluid circuit, sealed and stored as an archive for future reference if desired. A separate withdrawal passageway may be provided in the first container for withdrawing particles (which may include some pathogens) concentrated therein. In such an embodiment, the umbilicus 64 could include an additional passageway and one of the pumping stations 56 could be devoted to withdrawing particles from the container.

If chambers or subchambers are connected in the fluid circuit in a parallel arrangement, processing time for a given quantity of fluid may be significantly reduced over the series or single chamber arrangements. This parallel arrangement also provides the advantage of one chamber for immediate testing and a second chamber which could be severed, sealed and stored for future testing, verification or other purposes.

A series arrangement may have further advantages in separating small pathogens. As illustrated in FIG. 2, after the first chamber, a sedimentation or separation enhancing agent, such as an affinity agent, for example, a chemical enzyme, may be added to the supernatant from the first chamber (which potentially contains the pathogens that the user desires to concentrate) to enhance sedimentation of the pathogenic organisms during processing in the second chamber or stage. Such an affinity agent could be provided in a pre-attached container, as part of the disposable fluid circuit with fluid flow tubing communicating between the container and the fluid flow path between the first and second chambers or stages, or the disposable fluid circuit could have a facility such as an injection site or the like that permits user addition of a selected affinity agent into the flow path. Centrifuges with multiple pumps or pumping stations have the flexibility to permit one of the pumps to be used for automatically controlling the flow rate of such an affinity agent into the second chamber or into the supernatant flow path upstream of the second chamber according to a pre-selected or user-selected flow rate.

Although the present invention has been described in its preferred and alternative embodiments, it is contemplated that further alternatives will be apparent to one skilled in the field upon reading this specification, and the that the scope of the present invention is as defined in the appended claims, and not limited to the features or details of the illustrated embodiments unless expressly required by the appended claims.

That which is claimed:

1. A method for concentrating and recovering pathogens from fluid, comprising the steps of:
   continuously feeding the fluid through a flexible centrifugation chamber,
   subjecting the centrifugation chamber to centrifugal forces by rotating said chamber about a rotational axis while fluid is being fed therethrough to concentrate in said chamber pathogens contained in the fluid, and
   shaking the chamber to re-suspend pathogens concentrated in the chamber.

2. The method of claim 1 which includes twisting the chamber.

3. The method of claim 1 in which the step of shaking is carried out manually.

4. The method of claim 1 in which the flexible centrifugation chamber is elongated, and fluid is introduced into the chamber at substantially one end thereof and withdrawn at substantially the other end thereof.

5. The method of claim 1 in which the flexible centrifugation chamber is elongated, and fluid is introduced into the chamber at substantially one end thereof and withdrawn at substantially the same end thereof after traversing the length of the container at least about twice.

6. The method of claim 1 in which said chamber is elongated and includes a transverse seal line dividing the chamber into at least two sub-chambers, each sub-chamber including an inlet and an outlet generally in proximity to said transverse seal line and a segment-defining seal line separating said inlet and outlet and defining first and second flow path segments for fluid passing through said subchamber.

7. The method of claim 1 in which said chamber is defined by pair of facing plastic sheets, each of which has a peripheral edge area, said sheets being sealed together along at least said peripheral area.

8. The method of claim 1 in which the fluid is water.

9. A method for concentrating and recovering pathogens from fluid, comprising the steps of:
   continuously feeding the fluid serially through a plurality of flexible centrifugation chambers,
   subjecting the centrifugation chambers to centrifugal forces by rotating said chambers about a rotational axis while fluid is being fed therethrough to concentrate in said chamber pathogens contained in the fluid, and
   shaking at least one of the chambers to re-suspend pathogens concentrated in the chamber.

10. The method of claim 9 including adding a sedimentation enhancing agent to the fluid after processing through a chamber.

11. The method of claim 9 in which each of the one and other containers includes a flow path through which the fluid is fed, and the flow path in said other chamber is of greater length than the flow path in said one chamber.

12. The method of claim 9 further comprising the step of sealing and storing one of the chambers.

13. A method for concentrating and recovering pathogens from fluid, comprising the steps of:
   continuously feeding the fluid through a flexible centrifugation chamber,
   subjecting the centrifugation chamber to centrifugal forces by rotating said chamber about a rotational axis while fluid is being fed therethrough to concentrate in said chamber pathogens contained in the fluid, and
   shaking the chamber to and fro to cause a bolus of fluid in said chamber to slosh back and forth, creating increased shear forces in said chamber and causing said chamber to flex outwardly as said bolus of fluid sloshes back and forth, to re-suspend pathogens concentrated in the chamber.

14. The method of claim 13 including removing concentrated particles from said chamber.

15. The method of claim 13 in which the fluid is thereafter fed through another chamber to concentrate pathogens therewith.

* * * * *